US 7,455,673 B2

(12) United States Patent
Gotfried (10) Patent No.: US 7,455,673 B2
(45) Date of Patent: Nov. 25, 2008

(54) INTRAMEDULLARY NAIL SYSTEM AND METHOD FOR FIXATION OF A FRACTURED BONE

(76) Inventor: Yechiel Gotfried, 10, Ben Guiron Avenue, 27000 Kiryat-Bialik (IL)

( * ) Notice: Subject to any disclaimer, the term of this patent is extended or adjusted under 35 U.S.C. 154(b) by 785 days.

(21) Appl. No.: 10/616,218

(22) Filed: Jul. 8, 2003

(65) Prior Publication Data

US 2005/0010223 A1      Jan. 13, 2005

(51) Int. Cl.
    *A61B 17/56*    (2006.01)
(52) U.S. Cl. .......................................... 606/62; 606/64
(58) Field of Classification Search .................. 606/62, 606/64, 65, 66, 67, 87, 89, 98; 403/348, 403/349
    See application file for complete search history.

(56) References Cited

U.S. PATENT DOCUMENTS

| 3,433,220 | A | * | 3/1969 | Zickel | 606/67 |
| 4,827,917 | A | | 5/1989 | Brumfield | |
| 5,032,125 | A | | 7/1991 | Durham et al. | |
| 5,454,813 | A | * | 10/1995 | Lawes | 606/62 |
| 6,235,031 | B1 | | 5/2001 | Hodgeman et al. | |
| 6,443,954 | B1 | | 9/2002 | Bramlet et al. | |
| 6,565,573 | B1 | | 5/2003 | Ferrante et al. | |
| 6,648,889 | B2 | * | 11/2003 | Bramlet et al. | 606/62 |
| 7,147,399 | B2 | * | 12/2006 | Viscount et al. | 403/349 |
| 2002/0151898 | A1 | | 10/2002 | Sohngen et al. | |
| 2002/0156473 | A1 | | 10/2002 | Bramlet et al. | |

FOREIGN PATENT DOCUMENTS

| EP | 0 521 600 A1 | 1/1993 |
| WO | WO 02/083015 A1 | 10/2002 |

* cited by examiner

*Primary Examiner*—Eduardo C. Robert
*Assistant Examiner*—Michael J Araj
(74) *Attorney, Agent, or Firm*—Frishauf, Holtz, Goodman & Chick, P.C.

(57) ABSTRACT

Apparatus for treating a fracture of a bone of a subject includes an intramedullary (IM) nail, adapted to be inserted in a medullary canal of the bone of the subject, and having a proximal head that defines at least one hole therethrough. The apparatus also includes a sleeve, which includes a locking mechanism, which locking mechanism is adapted to engage the hole when the sleeve is inserted in the hole, such engagement preventing rotational and longitudinal movement between the sleeve and the hole. In an embodiment, the apparatus includes a screw, the sleeve being adapted to slidably receive the screw.

14 Claims, 7 Drawing Sheets

INTRAMEDULLARY NAIL SYSTEM AND METHOD FOR FIXATION OF A FRACTURED BONE

FIELD OF THE INVENTION

The present invention relates generally to implantable devices for treating femoral fractures, and specifically to an intramedullary system for coupling bone portions across a fracture.

BACKGROUND OF THE INVENTION

Intramedullary (IM) nails are implantable devices used to stabilize fractures and allow for bone healing. IM nails are inserted into the medullary canal of the long bones of the extremities, e.g., the femur or tibia. Currently-used IM nails have a head region that generally includes at least one hole, transverse to the longitudinal axis of the nail, for receiving anchoring means, such as a screw, to secure the nail within the medullary canal, of the bone. Some such anchoring means include at least one sleeve, which passes through the transverse hole, and through which a screw assembly typically passes freely. A proximal end of the head region protrudes from the proximal end of the bone, to facilitate post-implantation access to the IM nail, if desired. The proximal end of the head region, which protrudes from the bone, is a continuous extension of the head region, not structurally or visually distinct from the more distal portion of the head region that includes the holes.

U.S Pat. No. 4,827,917 to Brumfield, which is incorporated herein by reference, describes an IM system including a screw and an intramedullary rod. The screw has a threaded portion and a smooth portion, and the rod has a head, stem and a longitudinal bore. There is at least one pair of coaxial holes through the stem, transverse to the longitudinal axis of the rod, for receiving first anchoring means, such as a nail, screw or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw so as to permit the threaded portion of the screw, in use, to engage the femoral head and to allow sliding compression of a femoral neck or intertrochanteric fracture.

U.S. Pat. No. 5,032,125 to Durham et al., which is incorporated herein by reference, describes an IM hip screw that includes an IM rod, a lag screw and a sleeve for slidably receiving the lag screw. The sleeve is received in a passage in the IM rod having an axis positioned at an angle relative to the longitudinal axis of the IM rod such that the axis of the sleeve is directed toward the head of the femur. The IM hip screw is described as permitting sliding compression of selected fractures, particularly intertrochanteric fractures and fractures of the femoral neck.

U.S. Pat. No. 6,443,954 to Bramlet et al., which is incorporated herein by reference, describes an IM system that includes a lag screw assembly extending through a radial bore in an IM nail. The lag screw is inserted into one portion of a bone and deployed to fix the leading end. The IM nail is placed in the IM canal of a portion of the bone and the trailing end of the lag screw assembly is adjustably fixed in the radial bore to provide compression between the lag screw assembly and the IM nail. The IM nail has a cap screw in the proximal end holding the lag screw assembly and a tang in the distal end. The tang has legs extending through the nail to fix the distal end in the IM canal.

U.S. Pat. No. 6,235,031 to Hodgeman et al., which is incorporated herein by reference, describes an IM system that includes an IM rod, a lag screw, and a lag screw collar. The rod has a proximal end with a transverse bore extending therethrough. The lag screw has a distal end with coarse bone engaging thread elements and a proximal end with screw threads. When in use, the lag screw is substantially axially aligned with the transverse bore of the rod. The lag screw collar has an outer diameter sized to rotatably fit within the transverse bore of the rod. The collar also has an inner diameter and internal screw threads adapted to cooperate with the screw threads of the proximal end of the lag screw. The lag screw collar may have an increased outer diameter at one end thereof which is at least slightly larger than a diameter of the transverse bore of the rod.

U.S. Patent Application Publication 2002/0151898 to Sohngen et al., which is incorporated herein by reference, describes an IM nail having a modular configuration, including a nail member having a chamber formed on the proximal end thereof. An insert having at least one opening therein for receiving a bone screw or fastener is disposed within the chamber and is secured therein by a locking ring. Various inserts are described for use to achieve selected bone screw or fastener configurations.

U.S. Patent Application Publication 2002/0156473 to Bramlet et al., which is incorporated herein by reference, describes an IM system that includes an IM nail for insertion in the femur. The nail has an axial bore and an intersecting transverse bore. A lag screw is inserted through the transverse bore and turned into the head of the femur. A slotted sleeve is inserted over the lag screw and through the transverse bore with the slots aligned with the axial bore. A sleeve lock is inserted into the axial bore, and has a locking tab which engages the slots in the sleeve preventing rotational and longitudinal movement between the sleeve and the nail. A compression screw is turned into the trailing end of the lag screw and engages the encircling sleeve to provide longitudinal translation between the lag screw and sleeve to apply compressive force across a fracture.

European Patent Application Publication EP 0 521 600 to Lawes, which is incorporated herein by reference, describes an IM system that includes an IM rod having an angulated opening to receive a femoral neck screw having a threaded portion at its distal end, and locking means acting between the neck screw and the wall of the angulated opening to prevent relative rotation between the screw and the rod.

PCT Publication WO 02/083015 to Ferrante et al., which is incorporated herein by reference, describes an orthopedic screw having a screw head, a screw body with a distal tip, a shank with an enlarged diameter at the trailing end and a thread extending radially outward from the shank, and an internal capture surface. The screw is used with an orthopedic implant system, which includes an orthopedic implant and a driver capable of engaging the internal capture of the screw.

SUMMARY OF THE INVENTION

In some embodiments of the present invention, an intramedullary (IM) system for implantation in a medullary canal of a femur of a subject, comprises an IM nail having a head and a stem. The head of the IM nail defines at least one hole, which is oriented in an angled direction toward the femoral head relative to the longitudinal axis of the IM nail. The head hole is adapted to receive a sleeve, which is adapted to slidably receive a screw, so as to permit a threaded portion of the screw to engage a femoral head of the subject and to allow sliding compression of a femoral neck or intertrochanteric fracture. The sleeve comprises a locking mechanism, which engages the head hole, preventing rotational and longitudinal movement between the sleeve and the head hole. The locking mechanism typically comprises a depressible male coupling element, such as a tab, configured so that when the sleeve is inserted into the head hole and properly aligned, the tab engages a female coupling element, such as a notch, located on the inner surface of the head hole, thereby locking the sleeve to the head hole.

In some embodiments of the present invention, an IM system comprises an IM nail having a head and a stem. The head of the IM nail comprises a distal portion, which typically includes at least one head hole, and a proximal portion, having a diameter less than a diameter of the distal portion. For some applications, the diameter of the proximal portion is less than about 50% of the diameter of the distal portion. Such a narrower proximal portion typically allows greater regrowth and healing of the neck of the femur towards the area of the greater trochanter, than generally occurs upon implantation of conventional IM nail heads. At the same time, because a proximal end of the narrower proximal portion generally remains easily locatable on the external surface of the femur in the area of the tip of the greater trochanter or the piriformis, a surgeon typically can readily locate the IM nail if post-operative access to the implant becomes necessary. For some applications, the IM system further comprises the sleeve locking mechanism described hereinabove.

In some embodiments of the present invention, an IM locating tool is provided for locating an IM nail, a proximal portion of which does not extend to the surface of the femur. Without the use of this IM locating tool, it is sometimes difficult for a surgeon to locate such an IM nail if post-operative access to the implant becomes necessary. To use the locating tool, the surgeon temporarily couples one or more connecting elements of the locating tool to respective head holes of the IM nail. As a result, a proximal end of the locating tool is positioned directly over the site on the surface of the femur at which the surgeon should drill.

It is noted that use of the term "head" with respect to the IM nail is intended to distinguish at least a portion of the proximal end of the nail from the stem of the nail. In some embodiments, the head is separated by a neck region from the stem, while in other embodiments, the head and stem are generally continuous.

There is therefore provided, in accordance with an embodiment of the present invention, apparatus for treating a fracture of a bone of a subject, including:

an intramedullary (IM) nail, adapted to be inserted in a medullary canal of the bone, of the subject, and including a proximal head that defines at least one hole therethrough; and a sleeve, including a locking mechanism, which locking mechanism is adapted to engage the hole when the sleeve is inserted in the hole, such engagement preventing rotational and longitudinal movement between the sleeve and the hole.

In an embodiment, the apparatus includes a screw, and the sleeve is adapted to slidably receive the screw.

In an embodiment, the proximal head is shaped so as to define a female coupling element located on a surface of the hole, and the locking mechanism includes a depressible male coupling element, configured to engage the female coupling element so as to prevent the rotational and longitudinal movement. For some applications, the female coupling element is shaped to define a notch. For some applications, the male coupling element includes a tab. For some applications, the depressible male coupling element is adapted to engage the female coupling element when the sleeve is inserted in the hole to a fixed depth and then rotated until the depressible male coupling element engages the female coupling element.

There is also provided, in accordance with an embodiment of the present invention, apparatus for treating a fracture of a bone of a subject, including an intramedullary (IM) nail, adapted to be inserted in a medullary canal of the bone of the subject, the IM nail including a proximal head having a distal portion and a proximal portion, the distal portion having a distal diameter, and the proximal portion having a proximal diameter less than or equal to about 80% of the distal diameter.

For some applications, the proximal diameter is less than or equal to about 50% of the distal diameter. For some applications, the proximal diameter is equal to between about 5 mm and about 10 mm and the distal diameter is equal to between about 11 mm and about 17 mm. For some applications, a length of the proximal portion is equal to between about 10% and about 50% of a length of the distal portion.

In an embodiment, the distal portion defines at least one hole therethrough, and including a sleeve, which includes a locking mechanism, which locking mechanism is adapted to engage the hole when the sleeve is inserted in the hole, such engagement preventing rotational and longitudinal movement between the sleeve and the hole.

There is further provided, in accordance with an embodiment of the present invention, apparatus for treating a fracture of a bone of a subject, including an intramedullary (IM) nail, adapted to be implanted in the bone, such that no portion of the IM nail extends to an external surface of the bone.

In an embodiment, the IM nail includes a proximal head that defines one or more proximal head holes therethrough, and including a locating device, which includes:

one or more connecting elements, fixed to a distal end of the locating device, the connecting elements adapted to be temporarily coupled to respective ones of the proximal head holes; and a location indicating element, fixed to a proximal end of the locating device, the location indicating element adapted to indicate, when the connecting elements are coupled to the holes, a location on the external surface of the bone substantially directly over a location of a proximal end of the proximal head.

For some applications, the one or more connecting elements include exactly one connecting element.

For some applications, each of the one or more connecting elements includes a locking mechanism, adapted to engage one of the proximal head holes when the connecting element is inserted in the proximal head hole, such engagement preventing rotational and longitudinal movement between the connecting element and the proximal head hole.

In an embodiment, the apparatus includes one or more sleeves, adapted to be coupled to respective ones of the proximal head holes, and the one or more connecting elements are adapted to be coupled to the respective ones of the proximal head holes by being coupled to respective ones of the sleeves when the one or more sleeves are coupled to the respective ones of the proximal head holes. For some applications, each of the one or more sleeves includes a locking mechanism, adapted to engage one of the holes when the sleeve is inserted in the hole, such engagement preventing rotational and longitudinal movement between the sleeve and the hole.

In an embodiment, the IM nail includes a proximal head having a proximal end, the proximal head defining at least one hole therethrough, and defining a longitudinal channel, open to the hole and to the proximal end, and the apparatus includes a bendable, resilient elongated element, which includes a sharp tip, the element adapted to be inserted (a) into the hole, (b) through at least a portion of the channel, (c) through the proximal end of the proximal portion, and (d) through the bone, so as to indicate a location on the external surface of the bone substantially directly over the proximal end of the proximal head. For some applications, the tip includes a screw thread. Alternatively, the tip includes a drill bit.

There is yet further provided, in accordance with an embodiment of the present invention, apparatus for locating an intramedullary (IM) nail implanted in a bone of subject, the IM nail having a proximal head that defines one or more, holes therethrough, the apparatus including:

one or more connecting elements, adapted to be disposed at a distal end of the apparatus, the connecting elements adapted to be temporarily coupled to respective ones of the holes; and a location indicating element, fixed to a proximal end of the apparatus, the location indicating element adapted to indicate, when the connecting elements are coupled to the holes, a location on an external surface of the bone substantially directly over a location of a proximal end of the proximal head, when no portion of the IM nail extends to the external surface of the bone.

For some applications, the one or more connecting elements include exactly one connecting element.

In an embodiment, each of the one or more connecting elements includes a locking mechanism, adapted to engage one of the holes when the locking mechanism is inserted in the hole, such engagement preventing rotational and longitudinal movement between the connecting element and the hole.

In an embodiment, the apparatus includes one or more sleeves, adapted to be coupled to respective ones of the holes, and the one or more connecting elements are adapted to be coupled to the respective ones of the holes by being coupled to respective ones of the sleeves when the one or more sleeves are coupled to the respective ones of the holes. For some applications, each of the one or more sleeves includes a locking mechanism, adapted to engage one of the holes when the sleeve is inserted in the hole, such engagement preventing rotational and longitudinal movement between the sleeve and the hole.

There is still further provided, in accordance with an embodiment of the present invention, apparatus for treating a fracture of a bone of a subject, including an intramedullary (IM) nail, adapted to be inserted in a medullary canal of the bone of the subject, the IM nail including a proximal head having a distal portion and a proximal portion, the proximal portion visually discrete from the distal portion, the proximal portion adapted to aid in locating the IM nail, and the distal portion adapted to be coupled to at least one element.

For some applications, the distal portion is adapted to be coupled to the at least one element, the at least one element being selected from the list consisting of: a nail, a screw, a pin, and a sleeve.

In an embodiment, the distal portion defines at least one hole therethrough, and including a sleeve, which includes a locking mechanism, which locking mechanism is adapted to engage the hole when the sleeve is inserted in the hole, such engagement preventing rotational and, longitudinal movement between the sleeve and the hole.

There is additionally provided, in accordance with an embodiment of the present invention, a method for treating a fracture of a bone of a subject, including:

inserting, in a medullary canal of the bone of the subject, an intramedullary (IM) snail having a proximal head that defines at least one hole therethrough;

insetting a sleeve in the hole; and locking the sleeve to the hole by moving the sleeve within the hole, so as to prevent rotational and longitudinal movement between the sleeve and the hole.

There yet additionally provided, in accordance with an embodiment of the present invention, a method for treating a fracture of a bones of a subject, including inserting, in a medullary canal of the bone of the subject, an intramedullary (IM) nail having a proximal head having a distal portion and a proximal portion, the distal portion having a distal diameter, and the proximal portion having a proximal diameter less than or equal to about 80% of the distal diameter.

There is still additionally provided, in accordance with an embodiment of the present invention, a method for treating a fracture of a bone of a subject, including implanting an intramedullary (IM) nail in the bone, such that no portion of the IM nail extends to an external surface of the bone.

There is also provided, in accordance with an embodiment of the present invention, a method for locating an intramedullary (IM) nail implanted in a bone of subject, the IM nail having a proximal head that defines one or more holes therethrough, the method including temporarily coupling one or more connecting elements to respective ones of the holes, in a manner that brings a location indicating element to a position from which the location indicating element indicates a location on an external surface of the bone substantially directly over a location of a proximal end of the proximal head, when no portion of the IM nail extends to the external surface of the bone.

For some applications, the method includes coupling the connecting elements to the location indicating element.

There is further provided, in accordance with an embodiment of the present invention, a method for locating an intramedullary (IM) nail implanted in a bone of a subject, the IM nail having a proximal head that has a proximal end, the proximal head defining at least one hole therethrough, the method including inserting a bendable, resilient elongated element, having a sharp tip, (a) into the hole, (b) through at least a portion of a longitudinal channel defined by the proximal head, the channel open to the hole and to the proximal end, (c) through the proximal end of the proximal portion, and (d) through the bone, so as to indicate a location on an external surface of the bone substantially directly over the proximal end of the proximal head, when no portion of the IM nail extends to the external surface of the bone.

There is yet further provided, in accordance with an embodiment of the present invention, a method for treating a fracture of a bone of a subject, including:

inserting, in a medullary canal of the bone of the subject, an intramedullary (IM) nail having a proximal head having a distal portion and a proximal portion, the proximal portion visually discrete from the distal portion;

positioning the proximal portion to aid in locating the IM nail; and coupling at least one element to the distal portion.

There is still further provided, in accordance with an embodiment of the present invention, apparatus for use with an intramedullary (IM) nail implanted in a bone of subject, the IM nail having a proximal portion and a distal portion that defines one or more holes therethrough, the apparatus including:

a support, adapted to be coupled to the proximal portion;

a pin, adapted to be inserted through, at any given time, one of the holes and into the bone in a vicinity of a fracture of the bone; and a multi-axial control element, adapted to be coupled to the support and to the pin, and to move the pin translationally and rotationally, so as to reduce and align the fracture, respectively.

Typically, the multi-axial control element includes a biaxial control element, which is adapted to move the pin in a cephalad direction and rotationally, so as to reduce and align the fracture, respectively.

In an embodiment, the biaxial control element includes a first member and a second member, both coupled to the support, the first and second members including a first set screw and a second set screw, respectively, the first and second set screws adapted to:

move the pin in the cephalad direction when both of the first and second set screws are rotated substantially simultaneously, and move the pin rotationally when exactly one of the first and second set screws is rotated.

For some applications, the biaxial control element includes a shaped element coupled to at least, one of the set screws, such that rotation of the at least one of the set screws in a first direction induces movement of the pin in the cephalad direction, and such that rotation of the at least one of the set screws in a second direction, opposite to the first direction, induces movement of the pin in the caudal direction.

The holes are typically elongated in parallel with a longitudinal axis of the IM nail.

There is also provided, in accordance with an embodiment of the present invention, apparatus for treating a fracture of a bone of a subject, including:

an intramedullary (IM) nail, adapted to be implanted in an intramedullary canal of the bone, the IM nail including a proximal portion and a distal portion that defines one or more holes therethrough; and an introducer, including:
a support, adapted to be coupled to the proximal portion;
a pin, adapted to be inserted through, at any given time, one of the holes and into the bone in a vicinity of the fracture; and
a multi-axial control element, adapted to be coupled to the support and to the pin, and to move the pin translationally and rotationally, so as to reduce and align the fracture, respectively.

There is additionally provided, in accordance with an embodiment of the present invention, apparatus for use with an intramedullary (IM) nail implanted in a bone of subject, the IM nail having a proximal portion and a distal portion that defines one or more holes therethrough, the apparatus including:

a support, includes means for coupling the support to the proximal portion;

a pin, adapted to be inserted through, at any given time, one of the holes and into the bone in a vicinity of a fracture of the bone; and means for moving the pin translationally and rotationally, so as to reduce and align the fracture, respectively.

In an embodiment, the means for moving the pin include means for moving the pin in a cephalad direction and rotationally, so as to reduce and align the fracture, respectively.

There is still additionally provided, in accordance with an embodiment of the present invention, a method for treating a fracture of a bone of a subject, the method including:

inserting an intramedullary (IM) nail in an intramedullary canal of the bone, the IM nail having a proximal portion and a distal portion that defines one or more holes therethrough;

inserting a pin through one of the holes and into the bone in a vicinity of the fractute;

temporarily coupling, via at least one intermediary element, a portion of the pin external to a body of the subject to the proximal portion of the IM nail; and moving the pin translationally and rotationally, so as to reduce and align the fracture, respectively.

The present invention will be more fully understood from the following detailed description of embodiments thereof, taken together with the drawings, in which:

DETAILED DESCRIPTION OF PREFERRED EMBODIMENTS

Figure 1:
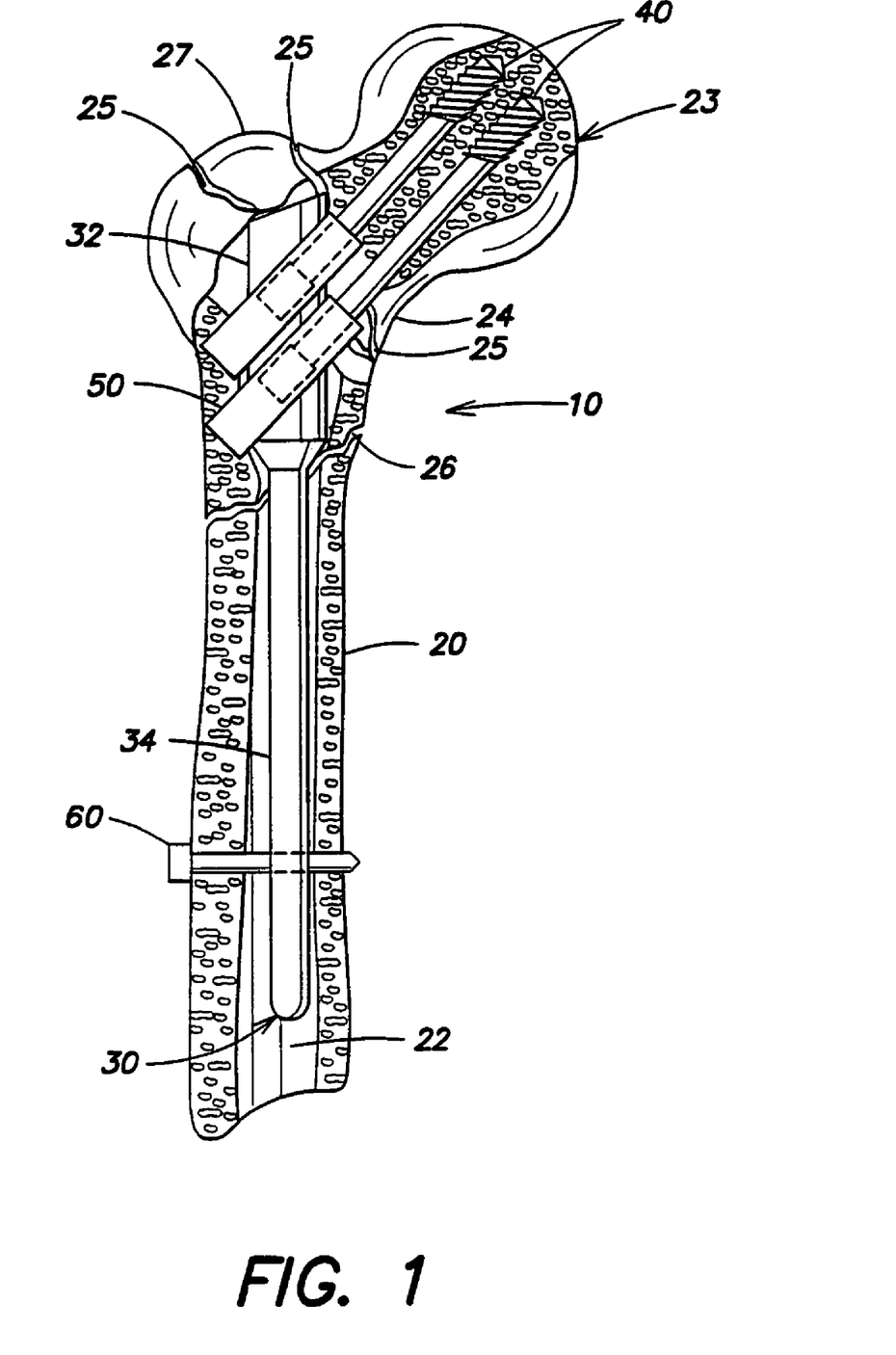
FIG. 1 is a schematic illustration of an intramedullary (IM) system in place in a femur, in accordance with an embodiment of the present invention.

FIG. 1 is a schematic illustration of an intramedullary (IM) system 10 in place in a femur 20, in accordance with an embodiment of the present invention. The IM system comprises an IM nail 30, having a proximal head 32 and a stem 34; at least one screw 40 for securing the IM nail at the head within a femoral head 23 of femur 20; and at least one sleeve 50. Alternatively, another anchoring element, such as a nail or bolt is used, instead of screw 40. IM system 10 typically further comprises at least one distal anchoring element 60, such as a screw, nail, or bolt, to secure IM nail 30 at stem 34 within a canal 22 of femur 20. For some applications, head 32 and/or stem 34 define a longitudinal bore (not shown).

Figure 2A:
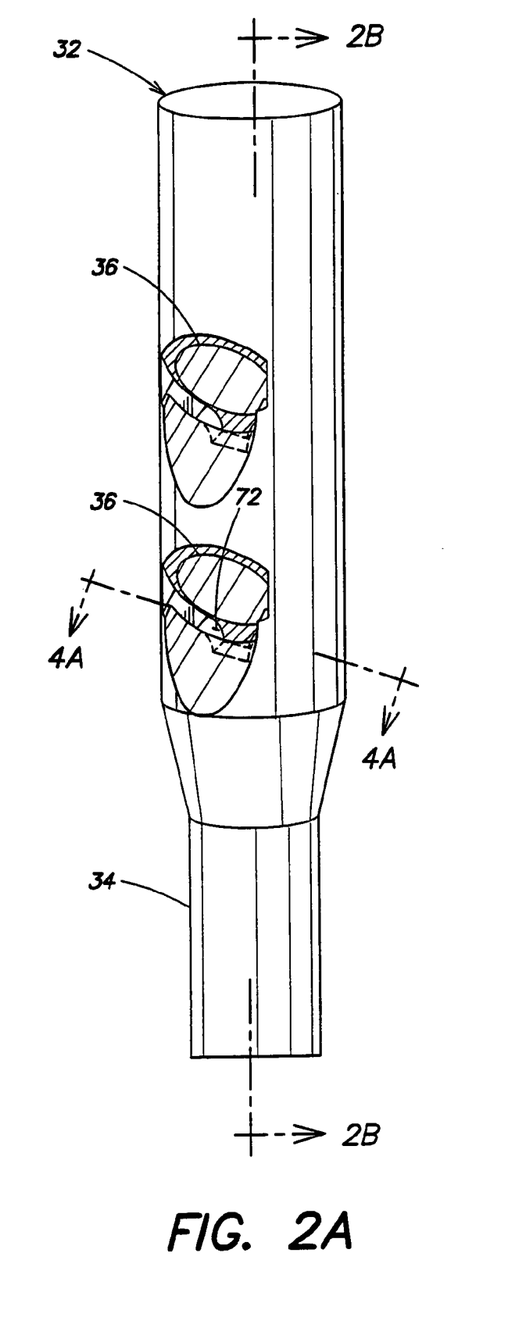
FIG. 2A is a schematic illustration of a head of the IM nail of FIG. 1.
Figure 2B:
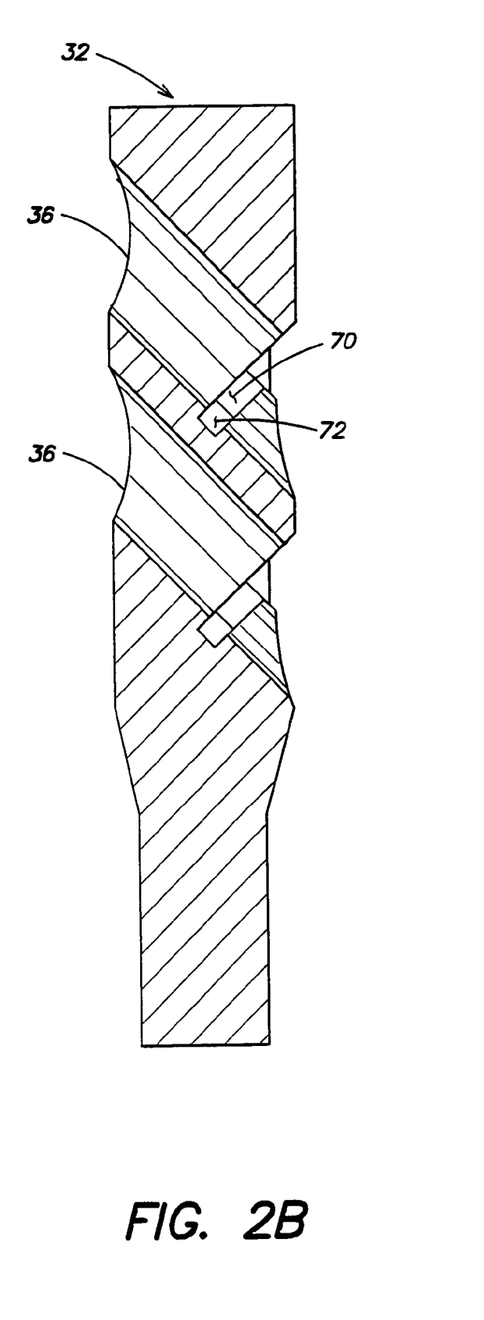
FIG. 2B is a cross-sectional illustration of the head through the line 2B-2B of FIG. 2A, in accordance with an embodiment of the present invention; 2A, in accordance with an embodiment of the present invention.

FIG. 2A is a schematic illustration of head 32 of IM nail 30, and FIG. 2B is a cross-sectional illustration of head 32 through the line 2B-2B of FIG. 2A, in accordance with an embodiment of the present invention. Head 32 defines at least one hole 36, typically two holes, as shown in the figures. Holes 36 are typically oriented in an angled direction toward a femoral head 23 (FIG. 1) relative to a longitudinal axis of IM nail 30.

Reference is again made to FIG. 1. In an embodiment of the present invention, head holes 36 are adapted to receive respective sleeves 50, which in turn are adapted to slidably receive screws 40, so as to permit a threaded portion of the screws to engage femoral head 23 and to allow sliding compression of a femoral neck 24, an intertrochanteric fracture 25, and/or a subtrochanteric fracture 26.

Figure 3:
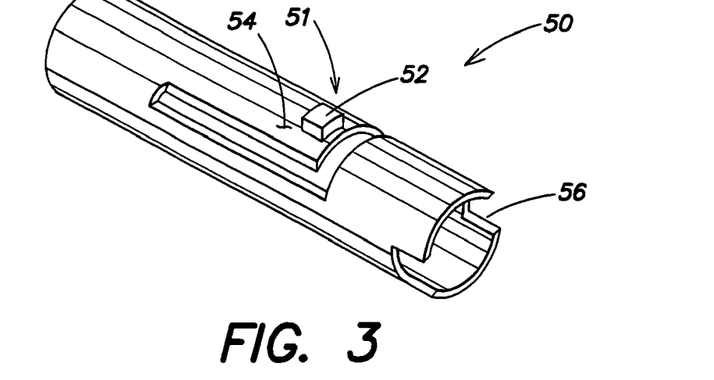
FIG. 3 is a schematic illustration of a sleeve for use with the IM system of FIG. 1, in accordance with an embodiment of the present invention.

FIG. 3 is a schematic illustration of sleeve 50, in accordance with an embodiment of the present invention. Sleeve 50 comprises a locking mechanism 51, which engages head hole 36, preventing rotational and longitudinal movement between sleeve 50 and head hole 36. The locking mechanism typically comprises a male coupling element, such as a tab 52 fixed to the outer surface of a depressible tongue 54, which is adapted to flex inwards toward the center of the sleeve when pressure is applied thereto. When the pressure is removed, tab 52 engages female coupling element, such as a notch 72 of hole 36, as described hereinbelow with reference to FIG. 4A. It is noted that in embodiments of the present invention, prevention of rotational and longitudinal movement between sleeve 50 and head hole 36 is not obtained by simply pressure-fitting the sleeve in the hole, or by simply screwing the sleeve in the hole, either of which generally would result in gradual loosening of the sleeve over time. In addition, sleeve 50 typically is shaped to define at least one cutout 56 to receive a screwdriver used by the surgeon to align the tab with the notch, as described hereinbelow with reference to FIGS. 4A and 4B.

Figure 4A:
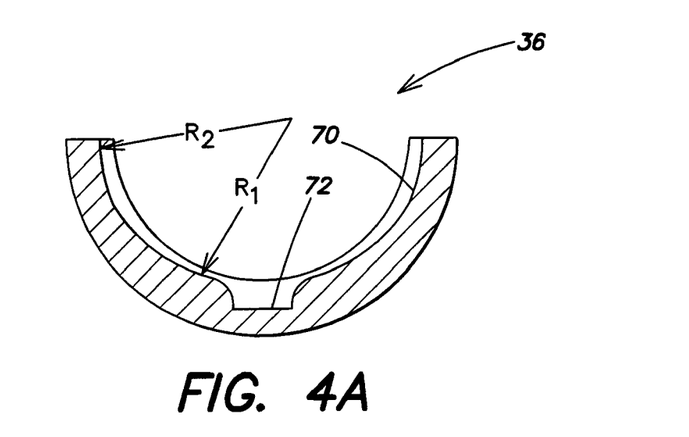
FIGS. 4A and 4B are cross-sectional illustrations of a head with one of the holes of FIG. 2A through the line 4A-4A of FIG. 2A, in accordance with embodiments of the present invention.
Figure 4B:
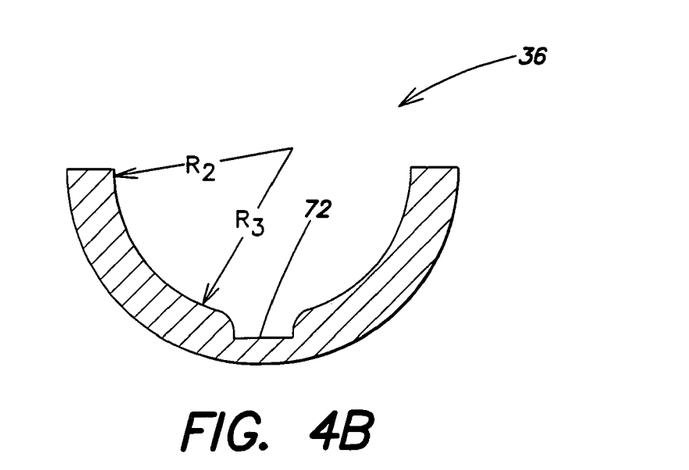

FIGS. 4A and 4B are cross-sectional illustrations of one of holes 36 of head 32 through the line 4A-4A of FIG. 2A, in accordance with an embodiment of the present invention. An inner grooved surface 70 of hole 36 is shaped to define a notch 72, which tab 52 engages when sleeve 50 is inserted into hole 36 and properly aligned, thereby locking sleeve 50 to hole 36. In the embodiment shown in FIG. 4A, the radius $R_1$ of grooved inner surface 70 adjacent to notch 72 is less than the maximum radius $R_2$ of inner surface 70 in a region further away from notch 72. To insert sleeve 50 into hole 36 and engage locking mechanism 51, the surgeon typically first rotationally orients the sleeve so that tab 52 is aligned with a region of hole 36 having maximum radius $R_2$, for example at the upper portion of hole 36. The surgeon then inserts the sleeve in the hole until tab 52 of sleeve 50 meets the upper portion of hole 36, which blocks further insertion of the sleeve. The surgeon then rotates the sleeve so that tab 52 approaches notch 72. As tab 52 approaches notch 72, tab 52 (and tongue 54) is gradually depressed by inner surface 70, until the tab reaches the notch and the tongue springs back into its original position, forcing the tab into the notch, and locking it therein. Such a locking mechanism is generally impervious to loosening under cyclical loading, even over the course of many years. By contrast, two pieces which are attached without a locking mechanism (e.g., by being screwed together or wedged together) are susceptible to gradual loosening over time.

In the alternate embodiment shown in FIG. 4B, the radius $R_3$ of inner surface 70 adjacent to notch 72 is substantially equal to the maximum radius $R_2$ of inner surface 70. Hole 36 in this alternate embodiment is typically flared, such that the tab is depressed during insertion of sleeve 50 into hole 36. Insertion of sleeve 50 into hole 36 in this alternate embodiment does not necessarily include rotation of sleeve 50 (as is described with reference to FIG. 4A).

Figure 5A:
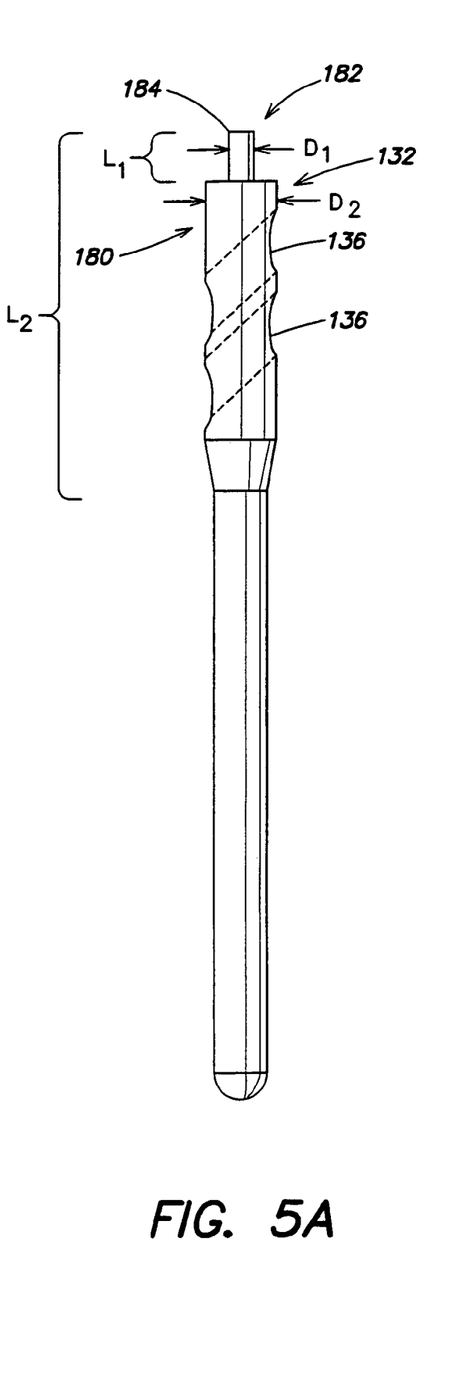
FIGS. 5A and 5B are schematic illustrations of a head of an IM nail, in accordance with embodiments of the present invention.

FIG. 5A is a schematic illustration of a head 132 of IM nail 30, in accordance with an embodiment of the present invention. In this embodiment, head 132 of IM nail 30 comprises a distal portion 180, which includes one or more head holes 136, and a proximal portion 182. Proximal portion 182 is adapted to aid in locating IM nail 30, while distal portion 180 is adapted to be coupled to at least one element, such as a nail, screw, or a sleeve. Proximal portion 182 is visually and structurally distinct from distal portion 180. Alternatively or additionally, proximal portion 182 has a diameter $D_1$ that is less than a diameter $D_2$ of distal portion 180 adjacent to proximal portion 182. For some applications, diameter $D_1$ is between 50% and about 80% of diameter $D_2$, or is less than about 50% of diameter $D_2$. For some applications, diameter $D_1$ is between about 25% and about 50% of diameter $D_2$. Typically, for IM nails intended for use in adults, diameter $D_1$ is between about 5 mm and about 10 mm, and diameter $D_2$ is between about 11 mm and about 17 mm. A length $L_1$ of proximal portion 182 is typically equal to between about 10% and about 50% of a length $L_2$ of head 132. For example, length $L_1$ may be between about 10 mm and about 35 mm, and length $L_2$ may be between about 40 mm and about 60 mm, in IM nails intended for use in adults. Although head 132 is shown in the figures as narrowing suddenly, for some applications the diameter of the head decreases gradually from $D_2$ to $D_1$. For some applications, such as for use in conjunction with the techniques, described hereinbelow with reference to FIGS. 6 or 7, (a) proximal portion 182 is removable, in which case the surgeon typically removes the proximal portion after implanting IM nail 30, or (b) head 132 does not comprise proximal portion 182, so that head 132 does not extend to the surface of femur 20.

Figure 5B:
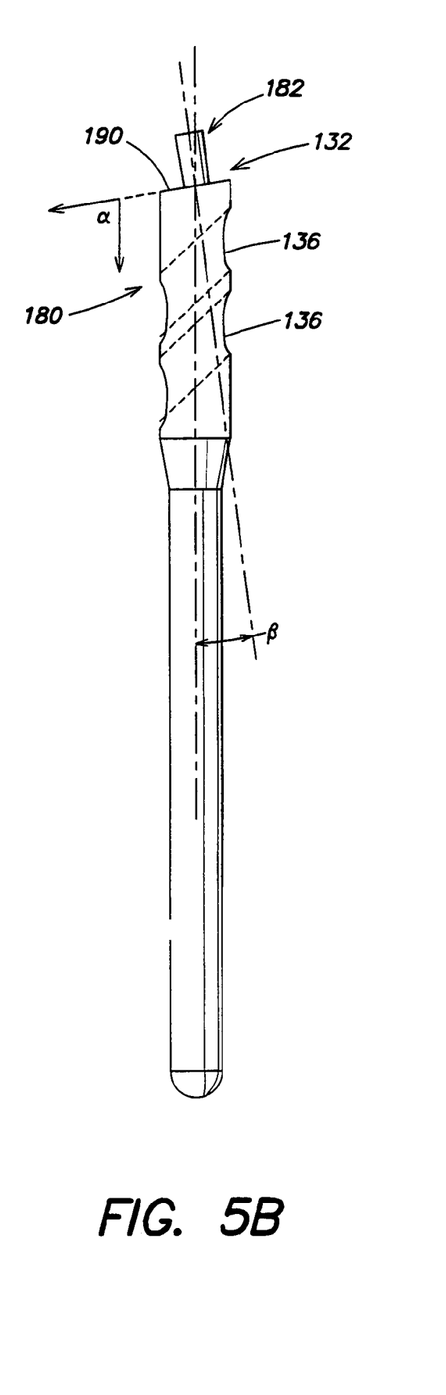

FIG. 5B is a schematic illustration of head 132 of IM nail 30, in accordance with an embodiment of the present invention. In this embodiment, a longitudinal axis of proximal portion 182 is oriehted at an angle β with respect to a longitudinal axis of distal portion 180. Angle β is typically between about 4 and about 40 degrees, in this embodiment. Optionally, a proximal surface 190 of distal portion,180 is oriented at an angle α with respect to the longitudinal axis of distal portion 180. Angle α is typically between about 4 and about 40.

During an implantation procedure, IM nail 30 is typically inserted into femur 20 so that a proximal end 184 of proximal portion 182 is generally flush with or slightly protrudes from a surface region 27 of femur 20 in a vicinity of the greater trochanter or the piriformis (FIG. 1) As a result, a surgeon generally can readily locate the IM nail if post-operative access to the implant becomes necessary. In addition, such a narrower proximal portion typically allows, greater regrowth and healing of the neck of the femur towards the area of the greater trochanter, than generally occurs upon implantation of conventional IM nail heads.

For some applications, IM nail 30 comprises both narrower proximal portion 182 and locking mechanism 51, as described hereinabove. For other application, the IM nail comprises only one of these features, but is generally otherwise conventional.

Figure 6:
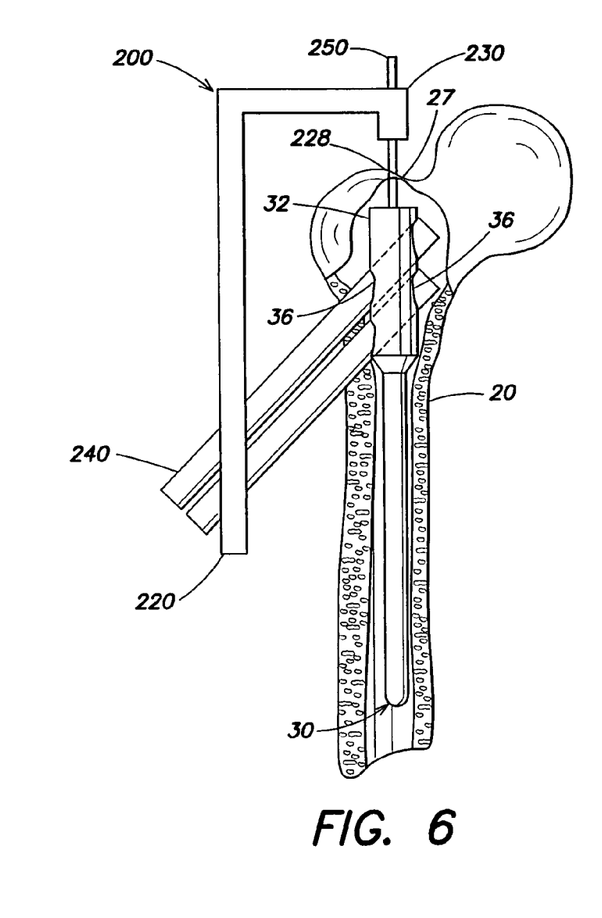
FIG. 6 is a schematic illustration of an IM locating tool, in accordance with an embodiment of the present invention.

FIG. 6 is a schematic illustration of an IM locating tool 200, in accordance with an embodiment of the present invention. In this embodiment, proximal portion 32 of IM nail 30 does not extend to surface region 27 of femur 20. Without the use of IM locating tool 200, it is sometimes difficult for the surgeon to locate proximal portion 32 of IM nail 30 if post-operative access to the implant becomes necessary. A distal end 220 of the locating tool comprises or is removably coupled to one or more connecting elements 240, which typically comprise a locking mechanism similar to locking mechanism 51, for locking to IM nail 30, as described hereinabove with reference to FIG. 3. Alternatively, connecting elements 240 comprise another locking mechanism such as protrusions, clips, or pegs.

To use the locating tool, the surgeon temporarily couples connecting elements 240 to respective head holes 36 of IM nail 30. For some applications, the surgeon performs this coupling by removing any sleeves or screws present in holes 36, and inserting a sleeve (not shown), which may be similar to sleeve 50 described hereinabove with reference to FIG. 3, into each hole 36. The surgeon then couples each connecting element 240 to one of the sleeves. Alternatively, connecting elements 240 are directly coupled to head holes 36. In either case, after the connecting elements are in a fixed position with respect to IM nail 30, tool 200 is typically placed or slid onto the connecting elements, so as to assume a known, rigid position with respect thereto. (In embodiments in which connecting elements 240 are an integral part of tool 200, this step is not necessary.) The use of at least two connecting elements 240 provides for a known, fixed orientation of IM locating tool 200 with respect to IM nail 30. For applications that use only a single connecting element 240, means are provided for ensuring a fixed rotational angle between connecting element 240 and hole 36, thereby providing a known, fixed orientation of IM locating tool 200 with respect to IM nail 30. For example, such means may include a slot in hole 36.

Typically, coupling IM locating tool 200 to IM nail 30 automatically positions a proximal end 230 of the locating tool so as to indicate a site 228 of surface region 27 substantially directly over proximal portion 32 of the IM nail. The surgeon typically uses knowledge of the location of site 228 in order to determine an appropriate location at which to drill. For some applications, proximal end 230 comprises means for guiding a marking device 250 or drill, such as a hole through which the marking device or drill is inserted.

Figure 7:
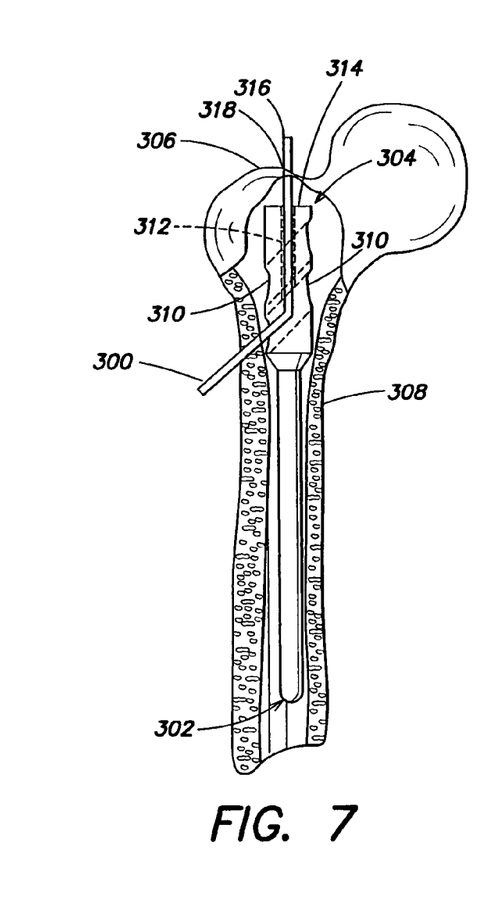
FIG. 7 is a schematic illustration of another IM locating tool, in accordance with an embodiment of the present invention.

FIG. 7 is a schematic illustration of an IM locating tool 300, in accordance with an embodiment of the present invention. An IM nail 302 comprises a proximal portion 304 which does not extend to a surface region 306 of a femur 308. The proximal portion defines one or more head holes 310, and a longitudinal channel 312 open to at least one of the head holes and to a proximal end 314 of proximal portion 304. Without the use of IM locating tool 300, it is sometimes difficult for the surgeon to locate proximal portion 304 of IM nail 302 if post-operative access to the implant becomes necessary.

IM locating tool 300 comprises an elongated element that is both bendable and resilient, i.e., is able to bend while maintaining longitudinal strength. A tip 316 of tool 300 is sufficiently sharp to pass through femur 308. In order to locate a site 318 of surface region 306 substantially directly over proximal portion 304 of the IM nail, the surgeon inserts tool 300, sharp end first, into one of head holes 310. The surgeon guides the tool through channel 312, so that the tool bends to conform with the channel. After pushing the tool so that tip 316 reaches the end of channel 312 at proximal end 314, the surgeon continues to push with sufficient force so that tip 316 punches through femur 308 and emerges from surface region 306 at site 318, thereby externally indicating the location of the site. Alternatively, tip 316 is threaded, and the surgeon rotates tool 300 so as to screw tip 316 through femur 308. Further alternatively, tool 300 comprises a flexible drill bit, and the surgeon drills the tool through femur 308. The surgeon typically uses knowledge of the location of site 318 attained through use of tool 300 in order to determine an appropriate location at which to drill during post-operative access to the IM nail.

Figures 8, 8A:
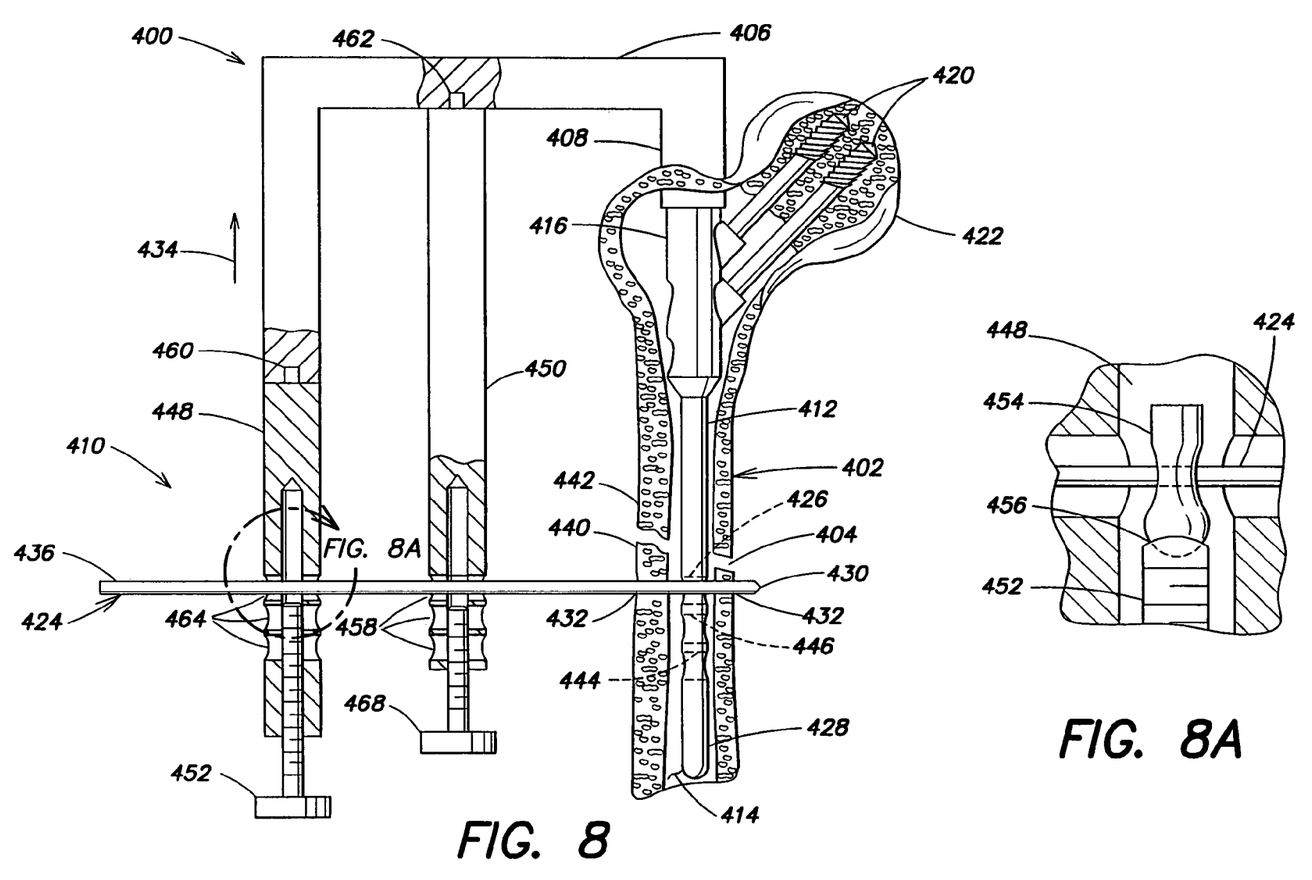
FIG. 8 is a schematic illustration of an introducer applied to a femur, in accordance with an embodiment of the present invention.
FIG. 8(A) is an enlarged view of the circled portion in FIG. 8.

Reference is now made to FIGS. 8 and 8A, which are schematic illustrations of an introducer 400 applied to a femur 402, in accordance with an embodiment of the present invention. Introducer 400 is adapted to actively reduce and align a fracture 404 of femur 402, such as a subtrochanteric fracture, while generally minimizing the required size of an incision in the vicinity of the fracture. Introducer 400 comprises a support 406, a coupling element 408, and a multi-axial control element, such as a biaxial control element 410. Coupling element 408 is adapted to couple introducer 400 to an IM nail 412, which is inserted into a medullary canal 414 of femur 402. For example, coupling element 408 may comprise a male element adapted to be inserted into a hole defined by a proximal end of a proximal head 416 of IM nail 412. Other coupling mechanisms used by conventional introducers may also be used. One or more neck screws 420 secure the IM nail at the head within a femoral head 422 of femur 402. Introducer 400 is typically shaped so as to define one or more holes (not shown) for guiding respective neck screws 420 during their insertion into femoral head 422.

Introducer 400 is shaped to facilitate use with a pin 424. During a procedure (which is generally performed using real-time imaging, such as fluoroscopy), pin 424 is inserted through femur 402 and through an elliptical or otherwise elongated hole 426, defined by a distal region 428 of IM nail 412 in a vicinity of fracture 404, such that the fracture is between the pin and coupling element 408. For some applications, pin 424 is threaded in a vicinity of a bone-penetrating tip 430 thereof and/or in a vicinity of one or both regions 432 thereof that pass through femur 402. Pin 424 typically has a diameter of between about 3 and about 6 mm, typically between about 4 and about 5 mm.

Figure 9A:
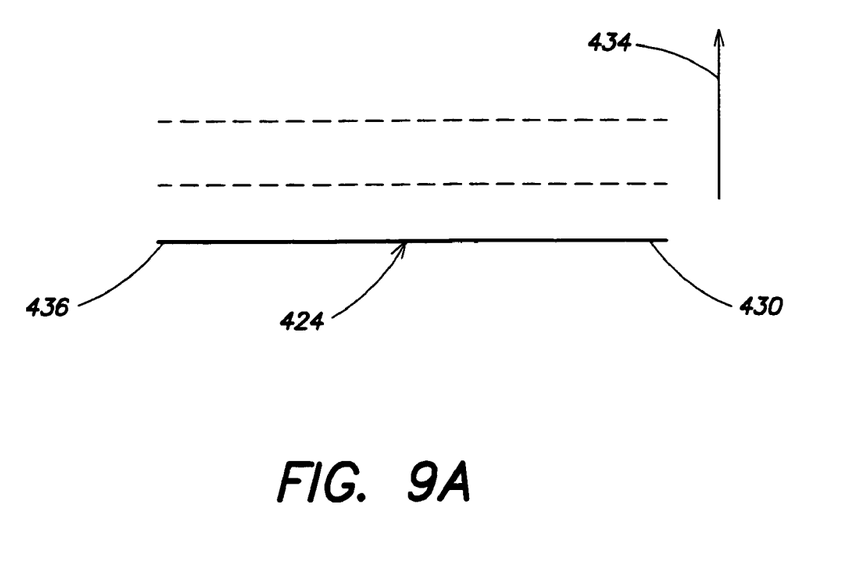
FIGS. 9A and 9B are schematic illustrations of motion of a pin of the introducer of FIG. 8, in accordance with an embodiment of the present invention.
Figure 9B:
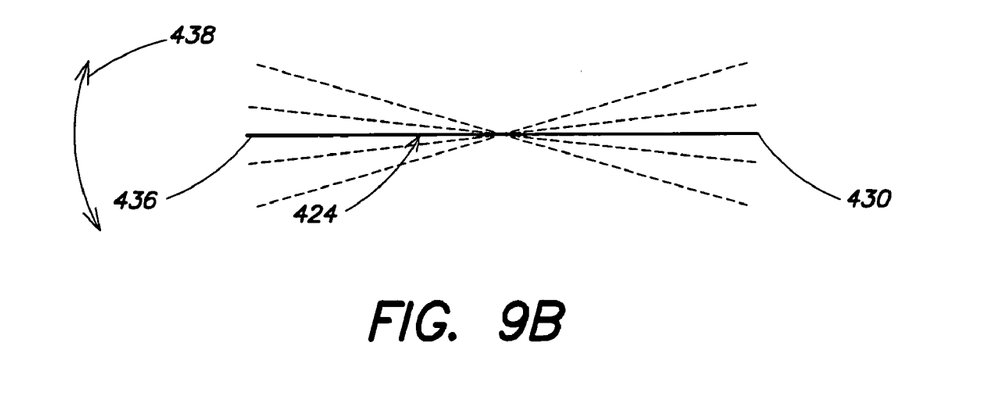

Reference is now made to FIGS. 9A and 9B, which are schematic illustrations of motion of pin 424, in accordance with an embodiment of the present invention. Biaxial control element 410 is adapted to move pin 424 along two axes, as follows:

- translationally, for example, in a cephalad direction toward support 406 (i.e., in the direction generally, indicated by arrow 434). In this manner, bone-penetrating tip 430 and a physician-manipulated end 436 of pin 424 generally move equal distances (FIG. 9A). Such cephalad movement serves to reduce fracture 404; and
- rotationally, such that bone-penetrating tip 430 and physician-manipulated end 436 move in opposite directions, i.e., tip 430 moves closer to or further away from support 406 in one of the directions generally indicated by arrow 438, while end 436 moves in the opposite direction (FIG. 9B). Such rotational movement serves to properly align fragments 440 and 442 of femur 402 with one Another (FIG. 8).

Elongated hole 426 typically has a length of about 10 mm to about 12 mm. Pin 424 is typically inserted through elongated hole 426 near a distal end thereof, which allows substantial rotation and cephalad motion of the pin before the pin comnes in contact with a proximal end of the hole, e.g., about 10 mm of motion. (FIG. 8 shows the pin already at the proximal end of hole 426.)

Reference is again made to FIG. 8. After fracture 404 has been reduced and aligned, a screw (not shown) is typically screwed through a hole 444, defined by dqistal region 428 of IM nail 412, into fragment 440, in order to fix IM nail 412 to fragment 440. Holes 444 is typically circular and positioned distally to elongated hole 426 (as shown), or proximal thereto (configuration not shown). Pin 424 is then removed from elongated hole 426. Optionally, a second screw (not shown) is screwed through elongated hole 426 into fragment 440 to further fix the IM nail to the fragment.

In an embodiment of the present invention, distal region 428 of IM nail 412 defines a secondary elliptical or otherwise elongated hole 446, in a distal vicinity of elongated hole 426.

In this embodiment, after removal of pin 424 from elongated hole 426, the pin is inserted through secondary hole 446. Biaxial control element 410 further moves pin 424 in the cephalad direction towards support 406, in order to further reduce fracture 404. Typically, about 10 mm of reduction is performed using elongated hole 426, and up to about an additional 10 mm of reduction is performed using secondary elongated hole 446, for a total reduction of up to about 20 mm. It has been the inventor's experience that fractures rarely require reduction of more than about 20 mm, after initial reduction with a fracture table.

In an embodiment of the present invention, biaxial control element 410 comprises a first member such as a first leg 448, and a second member such as a second leg 450, the first and second members comprising set screws 452 and 468, respectively. The first and second legs each define one or more elliptical or otherwise elongated holes 464 and 458, respectively. When inserted into elongated hole 426 of IM nail 412, pin 424 passes through one of holes 464 and one of holes 458. The pin is initially positioned near respective distal ends of the holes. Tightening set screw 452 pushes the pin towards a proximal end of the one of the holes 464, while tightening set screw 468 pushes the pin towards a proximal end of the one of the holes 458. Therefore:

tightening both set screws to the same extent and substantially simultaneously moves pin 424 in the cephalad direction towards support 406;

tightening only set screw 452 rotates pin 424 clockwise, in order to align fragments 440 and 442; and tightening only set screw 468 rotates pin 424 counterclockwise, in order to align fragments 440 and 442;

Typically, a combination of such tightening motions is performed in order to reduce and align fracture 440. It is noted that for some configurations (such as that shown in FIG. 8), tightening one of the set screws also induces some net cephalad motion of the center of pin 424. For some applications, one or both of legs 448 or 450 are removably coupled to support 406 by coupling elements 460 or 462, respectively (e.g., comprising screws or clips). For example, leg 450 may be removably coupled to support 406, in which case leg 448 and support 406 are used to insert IM nail 412 into intramedullary canal 414. The absence of leg 450 during this insertion generally makes introducer 400 easier to manipulate. After insertion of the IM nail, leg 450 is coupled to support 406.

In an embodiment, biaxial control element 410 comprises an optional shaped element, such as shaped element 454, coupled within biaxial control element 410 so as to provide means for pulling pin 424 (or otherwise inducing motion of pin 424) in the caudal direction. Shaped element 454 is coupled via a joint 456 to the proximal tip of set screw 452. (Alternatively or additionally, a shaped element is coupled to set screw 452.) Pin 424 passes through a hole in shaped element 454, such that joint 456 allows set screw 452 to rotate while shaped element 454 substantially does not rotate. In addition, joint 456 couples shaped element 454 and set screw 452 such that movement of either one along the proximal/distal axis induces movement of the other one in the same direction. In particular, distal (caudal) motion of set screw 452 causes corresponding caudal motion of pin 424. (By contrast, in embodiments not having shaped element 454 or equivalents thereof, proximal motion of set screw 452 causes cephalad motion of pin 424, while distal motion of set screw 452 does not induce any substantial motion of pin 424.) It is noted that the configuration and shape of shaped element 454 shown in FIG. 8 is by way of illustration and not limitation. A person of ordinary skill in the art of mechanical design, having read the disclosure of the present patent application, would be able to develop other substantially equivalent means for providing cephalad and caudal motion of pin 424.

In an embodiment of the present invention, introducer 400 is used in conjunction with a surgical plate having one or more elliptical or otherwise elongated holes through which pin 424 is inserted (configuration not shown). The plate is secured to the outside of femur 402 in a position suitable for reducing fracture 404 and for aligning fragments 440 and 442. For this embodiment, techniques described hereinabove with reference to FIGS. 8, 9A, and 9B are adapted to for use with the surgical plate, mutatis mutandis.

It will be appreciated that although some embodiments of the present invention have been shown and described herein for use in a femur, these embodiments may be adapted for use in other long bones of the extremities, such as the tibia and humerus, mutatis mutandis. It will also be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a fracture of a bone of a subject, comprising:
    an intramedullary (IM) nail, adapted to be inserted in a medullary canal of the bone of the subject, and comprising a proximal head that defines at least one hole therethrough, the intramedullary nail having a locking surface shaped to define an indent; and
    a sleeve, comprising a locking mechanism, wherein the locking mechanism comprises a depressible male coupling element, which engages the indent of the locking surface of the intramedullary nail when the sleeve is inserted in the hole so as to prevent rotational movement and both inward and outward longitudinal movement between the sleeve and the intramedullary nail.

2. Apparatus according to claim 1, comprising a screw, wherein the sleeve is adapted to slidably receive the screw.

3. Apparatus according to claim 1, wherein the male coupling element comprises a tab.

4. Apparatus according to claim 1, wherein the depressible male coupling element is adapted to engage the indent when the sleeve is inserted in the hole to a fixed depth and then rotated until the depressible male coupling element engages the indent.

5. Apparatus according to claim 1, wherein the depressible male coupling element comprises a depressible tongue.

6. Apparatus according to claim 5, wherein the depressible tongue includes a projection on an outer surface thereof which engages the indent of the locking surface of the intramedullary nail.

7. Apparatus according to claim 1, wherein the proximal head has a distal portion and a proximal portion, the proximal portion visually discrete from the distal portion, the proximal portion adapted to aid in locating the IM nail, and the distal portion adapted to be coupled to at least one element.

8. Apparatus according to claim 7, wherein the distal portion is adapted to be coupled to the at least one element, the at least one element being selected from the list consisting of: a nail, a screw, a pin, and a sleeve.

9. Apparatus according to claim 1, wherein the proximal head has a distal portion and a proximal portion, the distal portion having a distal diameter, and the proximal portion having a proximal diameter less than or equal to about 80% of the distal diameter.

10. Apparatus according to claim 9, wherein the proximal diameter is less than or equal to about 50% of the distal diameter.

11. Apparatus according to claim 9, wherein the proximal diameter is equal to between about 5 mm and about 10 mm and the distal diameter is equal to between about 11mm and about 17 mm.

12. Apparatus according to claim 9, wherein a length of the proximal portion is equal to between about 10% and about 50% of a length of the distal portion.

13. Apparatus according to claim 9, wherein the proximal portion of the head is removable from the distal portion of the head.

14. Apparatus according to claim 1, wherein the locking mechanism is integral with the sleeve.

* * * * *